(12) United States Patent
Reed

(10) Patent No.: US 9,993,603 B2
(45) Date of Patent: Jun. 12, 2018

(54) VALVED MEDICAL AEROSOL HOLDING AND DELIVERY CHAMBER

(71) Applicant: George Ashford Reed, Lake Oswego, OR (US)

(72) Inventor: George Ashford Reed, Lake Oswego, OR (US)

( * ) Notice: Subject to any disclaimer, the term of this patent is extended or adjusted under 35 U.S.C. 154(b) by 313 days.

(21) Appl. No.: 14/827,950

(22) Filed: Aug. 17, 2015

(65) Prior Publication Data

US 2017/0049976 A1 Feb. 23, 2017

(51) Int. Cl.
*A61M 11/00* (2006.01)
*A61M 15/00* (2006.01)

(52) U.S. Cl.
CPC ...... *A61M 15/009* (2013.01); *A61M 15/0015* (2014.02); *A61M 15/0018* (2014.02); *A61M 15/0023* (2014.02); *A61M 15/0086* (2013.01)

(58) Field of Classification Search
CPC ............ A61M 15/009; A61M 15/0005; A61M 15/0013; A61M 15/0015; A61M 15/0016; A61M 15/0018; A61M 15/0023; A61M 15/0086
USPC .......................... 128/200.14, 200.18, 200.23
See application file for complete search history.

(56) References Cited

U.S. PATENT DOCUMENTS

| | | | | |
|---|---|---|---|---|
| 5,660,167 A * | 8/1997 | Ryder | ..................... | A61M 11/06 128/200.14 |
| 5,813,401 A * | 9/1998 | Radcliff | .............. | A61M 16/208 128/200.14 |
| 6,039,042 A * | 3/2000 | Sladek | .............. | A61M 15/0086 128/200.23 |
| 6,363,932 B1 * | 4/2002 | Forchione | ......... | A61M 15/0086 128/200.14 |
| 6,631,721 B1 * | 10/2003 | Salter | ..................... | A61M 11/06 128/203.21 |
| 6,725,858 B2 * | 4/2004 | Loescher | .............. | A61M 16/08 128/200.14 |
| 2002/0121275 A1 * | 9/2002 | Johnson | ............ | A61M 15/0086 128/200.22 |
| 2003/0234015 A1 * | 12/2003 | Bruce | ............... | A61M 15/0086 128/200.23 |
| 2004/0250816 A1 * | 12/2004 | Kummer | .................. | A61D 7/04 128/205.25 |
| 2011/0232636 A1 * | 9/2011 | Von Hollen | ...... | A61M 15/0086 128/202.13 |
| 2012/0247460 A1 * | 10/2012 | Stenzler | ............ | A61M 15/0086 128/203.12 |

(Continued)

*Primary Examiner* — Kristen Matter
(74) *Attorney, Agent, or Firm* — Mark S Hubert

(57) ABSTRACT

A non linear, medicated aerosol holding and delivery chamber without sealing valves at the aerosol inlet and outlet ends. There is a low pressure actuated, vacuum relief, drain check valve at the bottom end of the chamber and an overpressure relief valve at the top end adjacent the mouthpiece opening. The vacuum relief, drain check valve has a radial support plate beneath it that allows for the creation of a vortex in the aerosol plume. The drain check valve also provides for the complete return of any condensed aerosol to the nebulizer when closed. The overpressure relief valve efficiently allows dispelling of the patient's air. Both valves aid in the decrease of the MMAD of the medicated aerosol particles. There is no truly enclosed volume defined by the body of the chamber as the mouthpiece is open into the top of the chamber body, free of any valves.

19 Claims, 6 Drawing Sheets

(56) References Cited

U.S. PATENT DOCUMENTS

2013/0276781 A1* 10/2013 Steelman .......... A61M 15/0086
128/203.12
2016/0101259 A1* 4/2016 Alizoti .............. A61M 16/0816
128/200.23

* cited by examiner

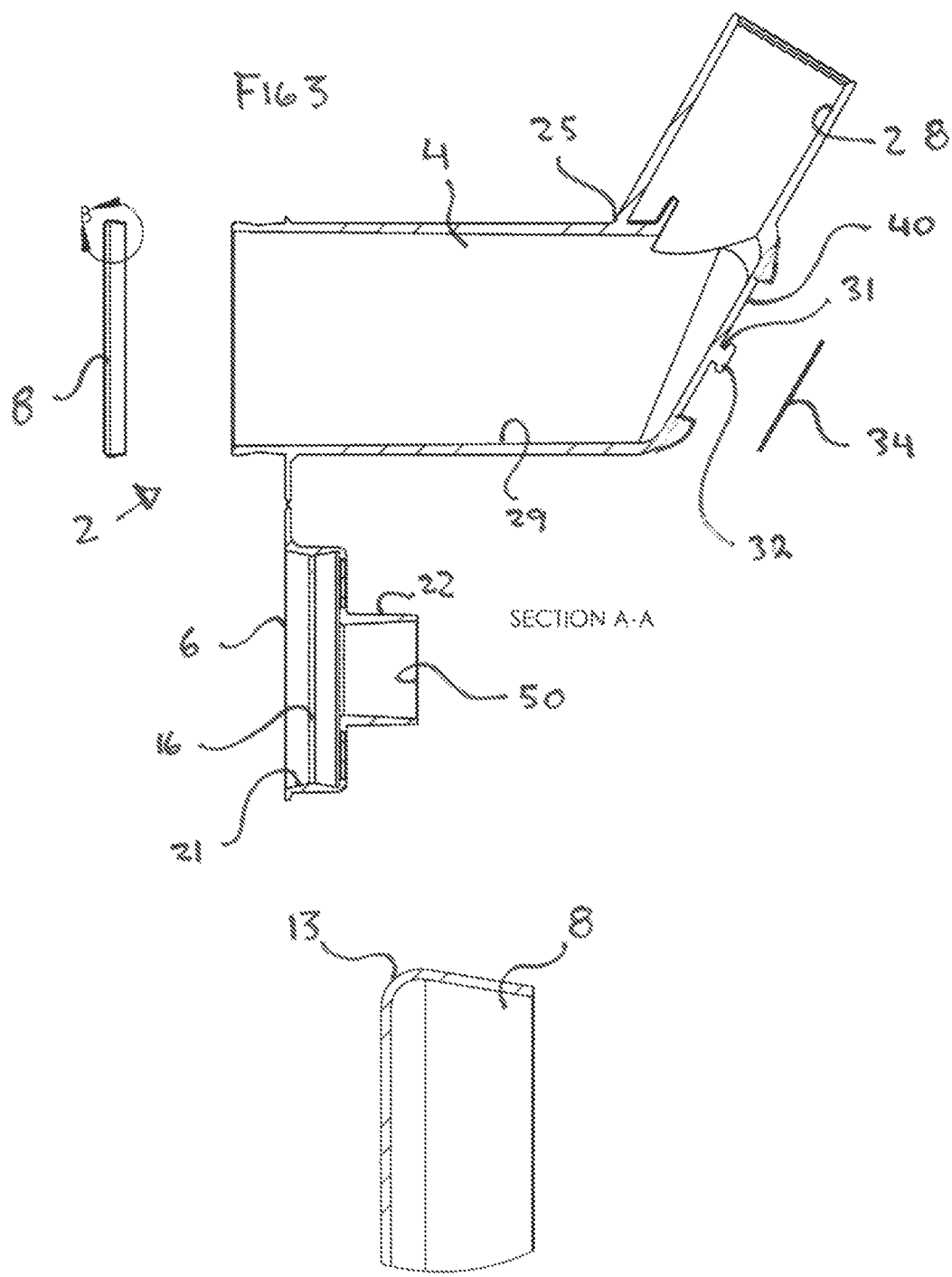

SECTION C-C

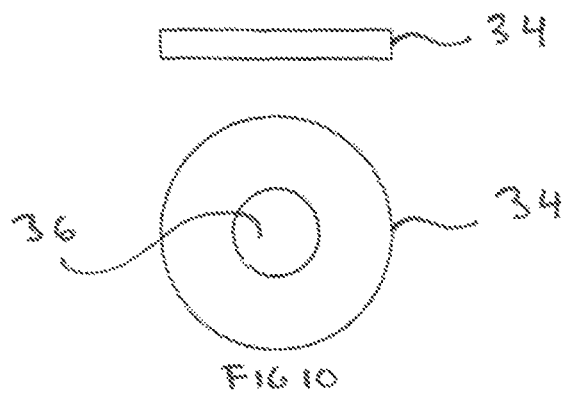
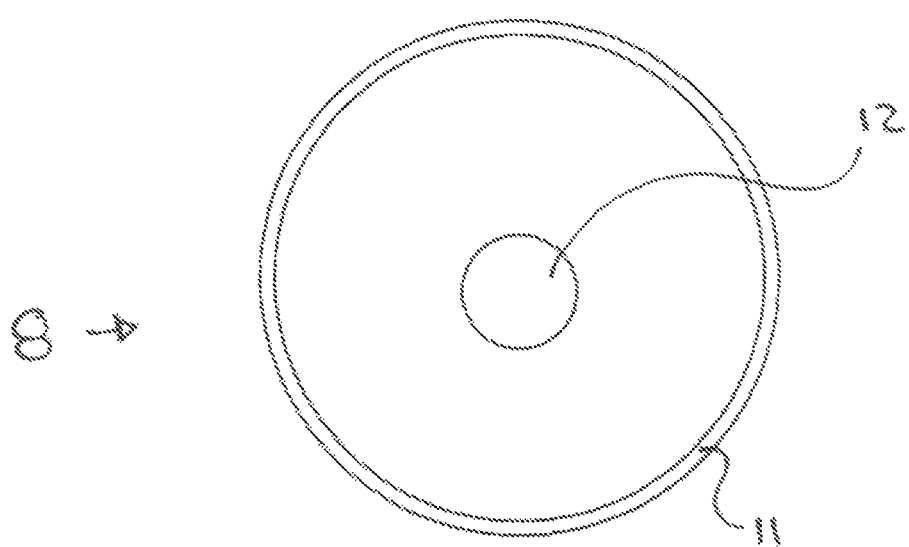

VALVED MEDICAL AEROSOL HOLDING AND DELIVERY CHAMBER

The present invention relates to a novel design for a medicated aerosol delivery device that introduces a new level of efficiency in both product delivery and device losses for those who need such treatments. It is adapted to matingly connect with various standardized pieces of related conventional aerosol generating equipment so as to allow enhanced respiratory treatments.

BACKGROUND OF THE INVENTION

Inhalation treatments for those with respiratory problems such as asthma or COPD generally involve the patient inhaling a medicated aerosol. This can be provided by a pressurized canister which atomizes and disburses the liquid medicine or by a nebulizer that atomizes the liquid medicine and allows it to separate and rise from the container of medicine. The atomization may occur through a variety of processes. The pressurized canister is generally used for quick, short bursts of medicine propelled into the lungs and is commonly known as a "metered dose inhaler", "rescue inhaler" or "puffer." The nebulizer is generally directed at longer respiratory treatments of 4-7 minutes in duration, and produces a slow moving aerosol plume that can be inhaled.

Of lately, while handy, the rescue inhalers have come under severe scrutiny for the non atmosphere friendly propellants that they employ. Changing the propellants from the traditional chlorofluorocarbon (CFC) to hydrofluoroalkane (HFA) a more atmosphere friendly gas, has dramatically driven up their cost. Many of the medical insurance companies will no longer cover the full cost of a rescue inhaler when they can be replaced by a nebulizer. For this reason nebulizers are now the aerosol delivery system of choice among medical providers.

However, nebulizers alone present problems as the efficiency varies widely from manufacture to manufacturer and have to be used with a holding chamber. The holding chamber is a vessel that allows the accumulation the aerosol plume and the subsequent release of this accumulation by the patient's inhalation. It helps ensure maximum delivery of medicine to the lower airways, and minimize the amount trapped on the back of the throat. Without a holding chamber to contain the generated aerosol plume, too much of the medicine is lost to the atmosphere. One of the problems with prior art holding chambers is minimizing the aerosol losses through escape and chamber wall condensation. Another problem is the unsanitary collection of the user's saliva within the chamber. However, the primary problem is getting the holding chamber to provide and enhance the percentage of correct sized aerosol particles for delivery.

Henceforth, an improved small volume nebulizer chamber that minimizes the aerosol losses, provides a concentration of the correct sized aerosol particles and aids in maintaining the chamber's sterility, would fulfill a long felt need in the respiratory treatment industry. This new invention utilizes and combines known and new technologies in a unique and novel configuration to overcome the aforementioned problems and accomplish this.

SUMMARY OF THE INVENTION

In accordance with the invention, the objects of the present invention, which will be described subsequently in greater detail, is to provide a non fully enclosed medical aerosol holding chamber that is able to connect to a plethora of standardized sized nebulizer outlets while optimizing the percentage of aerosol particles in the preferred size, minimizing the condensation losses on the internal surfaces of the body of the chamber, minimizing the condensation losses on any attendant valves within the chamber, decreasing the oropharyngeal deposition of the aerosol, delivering more aerosol to the lungs (particularly to the lower respiratory section), allowing condensed medicine to drain back from the chamber into the nebulizer body for re-atomization and minimizing the amount of saliva (drool) that can enter the chamber.

The nebulizer holding and delivery chamber has many of the advantages mentioned heretofore and many novel features that result in a new medicated aerosol delivery device which is not anticipated, rendered obvious, suggested, or even implied by any of the prior art, either alone or in any combination thereof.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements. Other objects, features and aspects of the present invention are discussed in greater detail below.

BRIEF DESCRIPTION OF THE DRAWINGS

FIG. 3 is an exploded cross sectional view of the chamber taken along Section Line A-A of FIG. 2;

FIG. 4 is an enlarged view of Detail B of FIG. 3;

FIG. 8 is a front view of the drain disc;

FIG. 9 is side cross sectional view of the drain disc;

FIG. 10 is a front view of the exhaust valve; and

FIG. 11 is a cross sectional side view of the exhaust valve.

DETAILED DESCRIPTION

Figure 1:
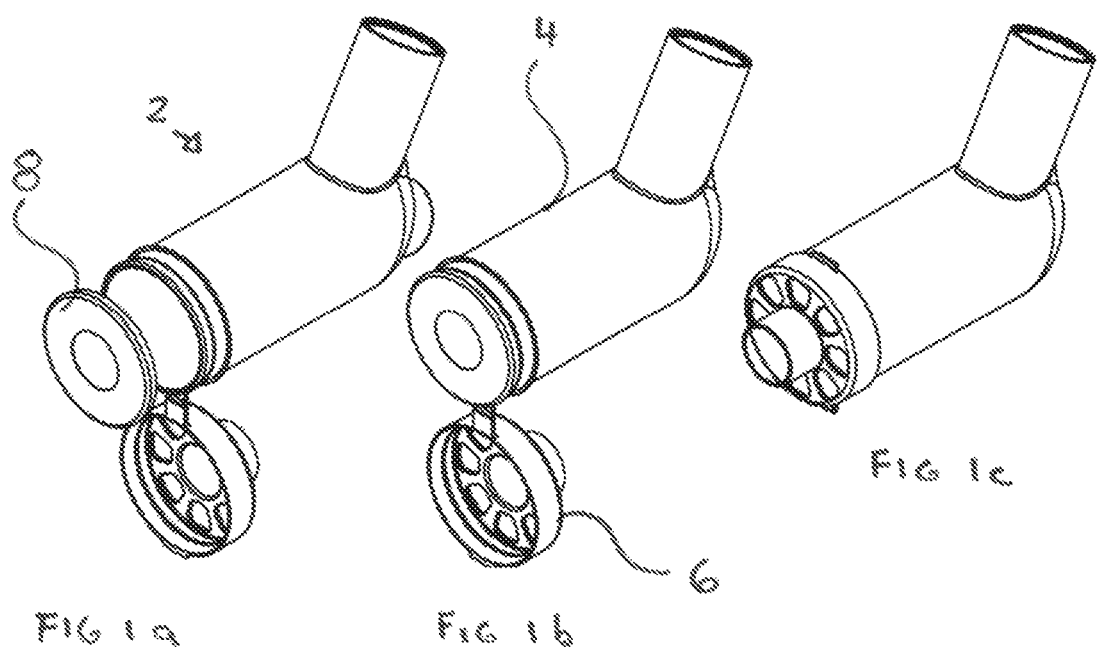
FIGS. 1a-c are front side perspective views of the chamber with the drain disc and the bottom sealing cap in various stages of assembly.

The above description will enable any person skilled in the art to make and use this invention. It also sets forth the best modes for carrying out this invention. There are numerous variations and modifications thereof that will also remain readily apparent to others skilled in the art, now that the general principles of the present invention have been disclosed.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As used herein, the term "MMAD" refers to the mass median aerodynamic diameter of the aerosol particles in the holding chamber. Results are established using an Andersen Cascade Impactor (ACI) averaging repeated readings over specified fill volumes. MMAD is and measured in microns. The optimum or required size for aerosolized particles to have a therapeutic significance is between 1 and 4.5 µm.

As used herein the term "GSD" refers to geometric stand deviation and is a dimensionless number that describes how spread out are a set of numbers whose preferred average is the geometric mean. With aerosol particles, the lower the GSD the more uniform in size the particles sampled are.

As used herein, the term "inhaled dose" refers to the amount of inhaled drug for a time interval of nebulization (generally one minute).

As used herein the term "drain mechanism" refers to a mechanical device that incorporates an internally opening vacuum relief, check drain valve that allows the return of condensed medication back to the source device (generally a nebulizer) and facilitates the entry of additional air into the delivery chamber as required by the patient's volume of inhalation.

As used herein, the term "exhalation mechanism" refers to a mechanical device that incorporates an externally opening valve that vents additional pressure from the delivery chamber at or near the source of the additional pressure.

Inhaled corticosteroids have been used with success by physicians for decades for the treatment of asthma and COPD. Nebulization is a common method for generating medical aerosol in a non propelled format that provides an easier alternative for children and older patients because of its easy-to-use delivery mechanism. Less of the medicine is lost on the throat and more of the medicine reaches to the lower respiratory region of the lungs as the velocity of the propelled aerosol is much lower and the mean particle size is much smaller. Studies have shown that use of a holding chamber or spacer, can increase the medicine delivery by as much as 36%. To allow optimal performance of a nebulizer, a holding chamber is positioned between the output of the nebulizer and the mouthpiece. This holding chamber collects the non pressurized plume of aerosol medicine and disperses it to the patient.

Generally, these holding chambers are hollow bodies have at a minimum, an inlet end (connected to the aerosol outlet of the nebulizer) and an outlet end (connected to the mouthpiece) and both ends. The most common nebulizer holding chambers are configured as a corrugated "T" piece, open at all three ends with the central arm connected to the nebulizer outlet. There are no valves in this design to constrain the nebulizer generated aerosol until inhalation. One of the arms serves as the mouthpiece inlet and the other exhaust arm allows room air to be drawn in with the nebulizer's generated aerosol on inhalation. Since the user's mouth remains in constant contact with the mouthpiece inlet, upon exhalation the exhaust arm serves as an exhaust vent. In this process much of the medicated aerosol is lost with the absence of valves and upon exhalation, much of the medicated aerosol is drawn out through the exhaust arm. Some of the aerosol drug particles discharged into a holding chamber are also lost to the chamber walls by inertial impaction, gravitational sedimentation, and electrostatic attraction to wall of the chamber. (The later two effects are accented with longer delay times.) These effects are minimized with larger-volume holding chambers.

The choice of material used in holding chambers used with rescue inhalers is a charge-dissipative (non-static) non-porous polymer, as this can be easily cleaned, and has minimal electrostatic attraction, which is of concern due to the polarity of the propellant, used in the rescue inhalers. With nebulizer holding chambers, there is no aerosol propellant and the polarity of the aerosol does not lend to considerable electrostatic attraction and good impact resistance. Since the valved aerosol holding chamber is intended as disposable or for single patient use, the material of construction need only be a non-porous, hypo allergenic polymer.

Because bacterial contamination of holding chambers is commonly introduced by the patient's saliva it is important that they be cleaned periodically. The less saliva that enters the device, the easier it is to clean.

Looking at FIGS. 1 a-c the valved holding chamber 2 can best be seen in three front side perspective views with the drain disc 8 and the bottom sealing cap 6 in various stages of assembly. In the preferred embodiment, it has an internal volume of approximately 104 cc, which is calculated to allow sufficient volume for aerosol plume dispersion while providing a good ratio of internal wall area to volume for minimizing condensation losses. Although other volumes may be employed, this size meets the operational and ergonomic criteria well. Changes in the volume will affect the MMAD of the aerosol particles exiting the mouthpiece of the valved aerosol holding chamber and entering the patient's lungs.

Looking at FIG. 3, it can be seen that the chamber 2 is comprised of four parts, a chamber body 4, a bottom sealing cap 6, an internally opening, internally mounted drain disc 8 and an externally opening, externally mounted exhaust valve 34. There is an optional mouthpiece (not illustrated) that frictionally fits onto the mouthpiece fitting section 9 on the chamber body 4. Functionally there is an exhalation mechanism and a drain mechanism each comprised of combinations of portions of the various four parts. The chamber 2 is non enclosed, that is to say that there is always a direct, unhampered pathway between the inlet and outlet end. The medicated aerosol is never fully enclosed within the chamber body 4.

Figure 2:
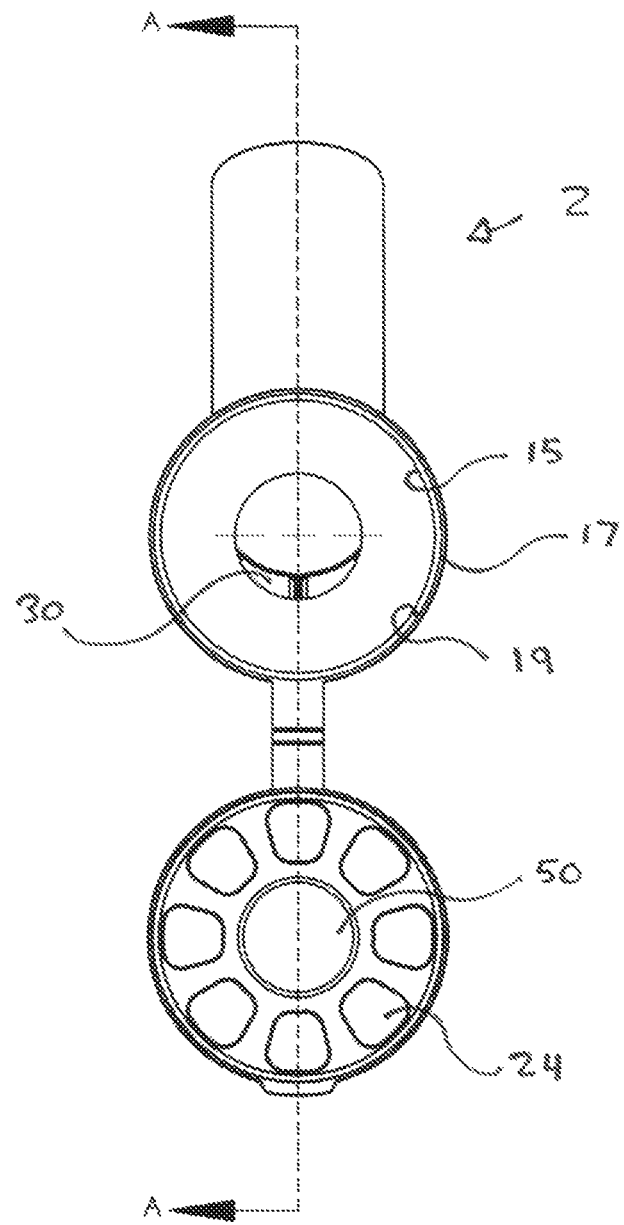
FIG. 2 is a front view of the chamber.

Looking at FIGS. 8 and 9, it can be seen that drain disc 8 in the preferred embodiment, is an internally mounted, centrally opening, circular disc check valve made of silicone or an equivalent flexible, polymer material having a raised flange 11 extending normally from its circular periphery. As shown in FIG. 4 the exterior edge of the drain disc 8 has a slight radius for ease of installation. The drain disc 8 is frictionally held in place on the distal end of the chamber. Here, there is a raised inner lip 15 that resides concentric to the outer surface 17 of the distal end of the chamber 2. (See FIG. 2) Between the inner lip 15 and the outer surface 17, there is a circular landing 19 that resides slightly behind the leading edge of the distal end 17 of the chamber 2. The drain disc 8 is positioned such that its raised flange 11 resides within the circular landing 19, and the circular inner edge of its face lies over the inner lip 15. When the bottom sealing cap 6 is frictionally affixed over the outer surface 17 of the distal end of the chamber 2, the drain disc 8 is pinned about its outer periphery in a leakproof manner by an inner peripheral flange 16 on the sealing cap 6 that firmly sandwiches the drain disc 8 between the cap 6 and the chamber body 4. The outer radius 13 on drain disc 8 prevents the crimping or tearing of the drain disc 8 as the bottom sealing cap 6 slides over it. As can be seen in FIG. 3, the bottom sealing cap 6 has a slight tapered inner leading edge 21 to allow for mating frictional engagement with the outer surface 17 of the distal end of the chamber 2. The drain disc 8 has a central orifice 12. It is known that other centrally opening mechanical valve designs may be utilized, however this design is economical, simple in operation, leakproof, easy to replace and not prone to failure. The drain mechanism is made of the drain disc 8, the inner lip, the circular landing 19 and the inner peripheral flange 16.

Figure 5:
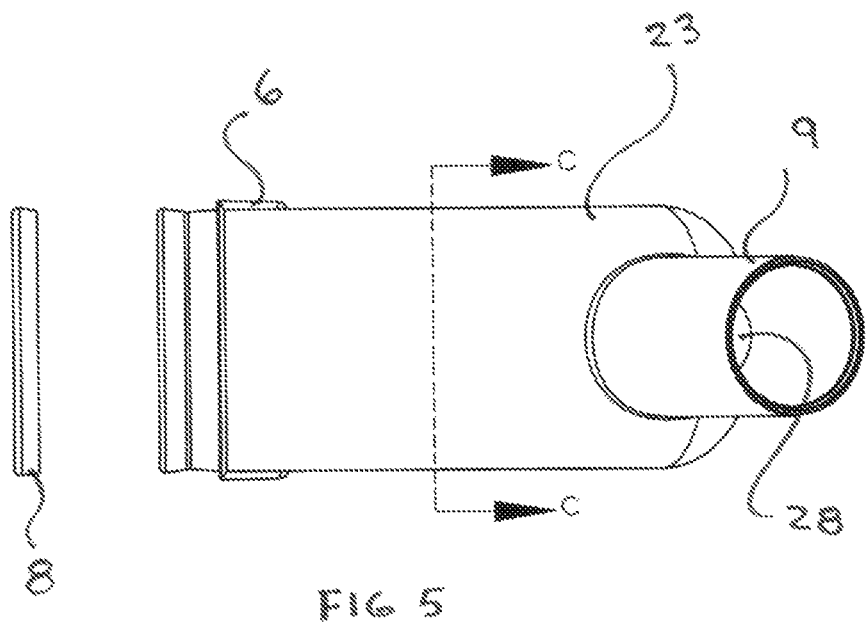
FIG. 5 is a top view of the chamber with the bottom sealing cap installed.

The non-linear obtuse angled chamber body has a generally circular axial cross sectional configuration with an open top mouthpiece fitting section 9 and an open bottom 28 (See FIG. 5). The mouthpiece fitting section 9 in the preferred embodiment is an external 22 mm diameter hollow stub shaft designed for frictional fit engagement with ISO standard 22 mm mouthpieces although other dimensions may be used. The mouthpiece (not illustrated) has an internal drip tray on the lower section to catch any of the saliva that may wander from the patient's mouth. This aids in sanitation and cleaning. Although designed to be a single patient use device, because bacterial contamination of holding chambers is commonly introduced by the patient's saliva it is important that they be cleaned periodically. The less saliva that enters the device, the easier it is to sterilize/clean. The internal drip tray prevents the migration of the patient's drool beyond the removable, washable mouthpiece.

The chamber body 4 has a "V" shaped configuration with two unequal length arms extending from the crouch of the "V". Each arm is generally circular in axial cross section, that is to say they may be circular tubes or any degree of oval tubes. The short, top arm 9 is the mouthpiece fitting section, (proximate end) and the longer, bottom arm 23 is the nebulizer inlet section (distal end) of the chamber body 4. The crouch or inner corner 25 of the chamber body has an obtuse included angle between the two arms of approximately 135 degrees. (Stated otherwise, the outer angle is between the two arms is approximately 225 degrees.) While other angles are possible the angle chosen (plus or minus 15 degrees) has shown to strike the best compromise between causing adequate inertial impact condensation to strip away aerosol particles greater than 5 um and enabling a sufficient volume of the vented release of exhaled air without loss of medicated aerosol.

Figure 6:
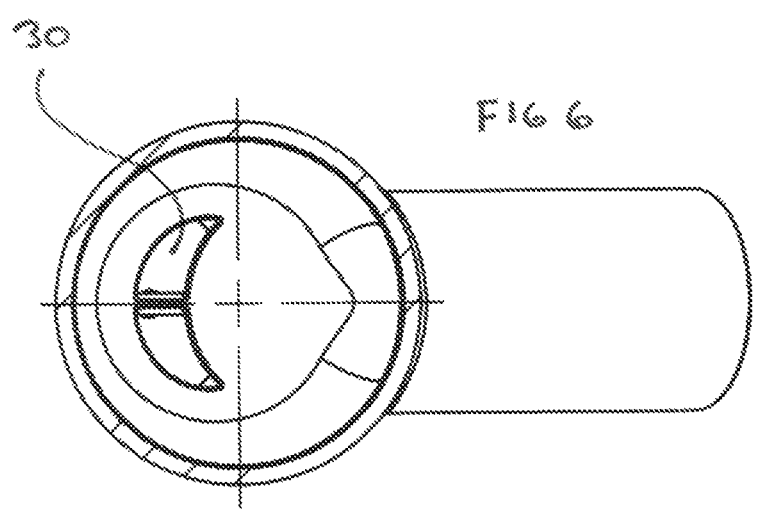
FIG. 6 is a cross sectional view of the chamber taken through section C-C of FIG. 5.

This "V" shape of a pathway for the medical aerosol serves six functions. First, it functions to make the inhaled medicated aerosol arc or turn to leave the chamber 2. The larger aerosol particles having a greater mass collide with the upper inner wall 28 and condense, leaving a higher ratio of the smaller, preferred aerosol particles under the 5 um diameter size. Studies have shown that the amount of concentration of 5 um and below aerosol particles may be increased by as much as 36% over that using the same nebulizer with the conventional corrugated "T" holding chamber detailed above. The second function is that the condensed particles on the upper, inner wall 28 then can run down the angled wall to return to the nebulizer via the drain mechanism rather than clinging to the ceiling of the conventional "T" configured chamber and not being able to return to the nebulizer until enough aerosol had condensed to form drops on the ceiling heavy enough to fall off. The third function is that the 135 degree crouch angle positions the exhalation mechanism in a direct line with the stream of air being exhaled by the patient, and at the top end of the accumulated medical aerosol plume in the chamber 2, thereby minimizing the amount of aerosol that the exhalation air draws out through the exhalation mechanism 10. The fourth function is that a minor portion of the exhaled air strikes the upper inner wall 28 about and adjacent the exhalation mechanism so as to be directed downward into the chamber cavity to create a swirling vortex in the accumulated charge, causing the larger aerosol particles to accelerate in the vortex of the medicated plume, and with their larger mass, strike the chamber lower inner wall 29 and condense. This also helps decrease the MMAD of the medicated aerosol particles in the holding chamber, getting more of them in the 5 um range. The fifth function is that "V" helps impart a laminar flow to the vortexed incoming charge of medicated aerosol allowing more of the smallest particles to concentrate in the central region of the inhaled charge thus increasing the chances of these smallest particles passing into the bottom third of the patient's lungs. The sixth function is that the design of the exhalation mechanism with the partially circular cut exhalation port 30 ensures that any escaping vapor is directed away from the patient's face or eyes. (See FIG. 6)

Figure 7:
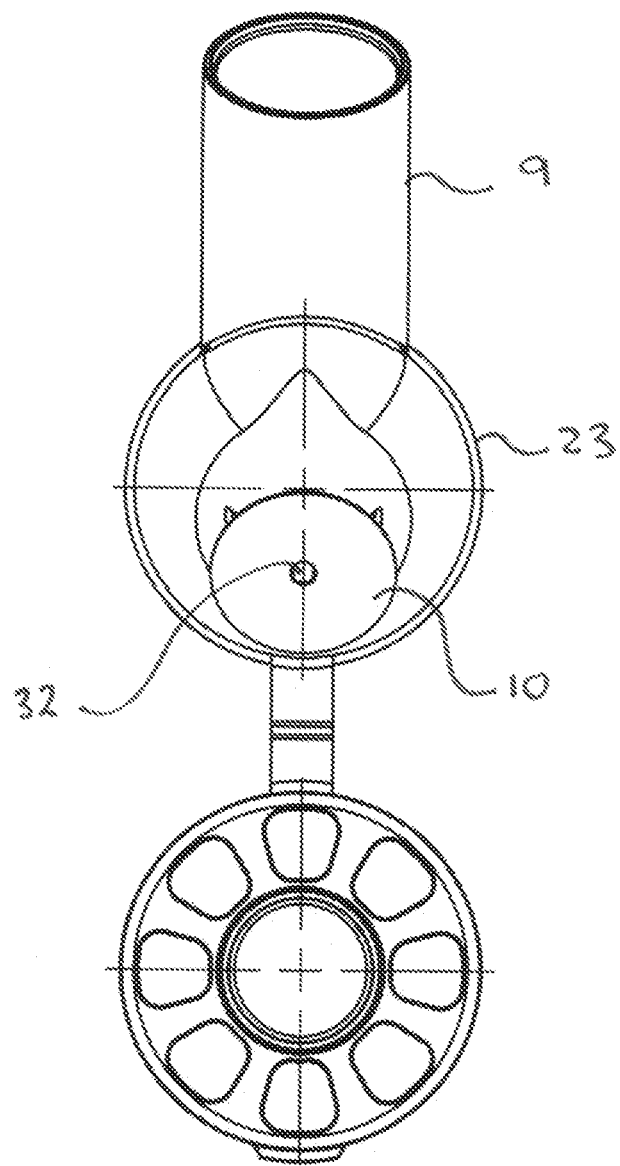
FIG. 7 is a back view of the chamber.

In the exterior face of the short top arm 9 is a depressed or reset circular region 40 sized to accommodate the overpressure relief exhaust valve 34 and an arced slot exhalation port 30 formed there through. Adjacent to the exhalation port 30 and extending normally from the outer face of the short top arm 9, is an exhaust mechanism retention post 32. In linear cross section, this post 32 has a "T" shape. The exhaust valve 34 is a circular, flexible polymer disc with a central orifice 36. In the preferred embodiment this would be made from silicon however there is a plethora of other flexible polymers that could be utilized as is well know in the art. The central orifice 36 of the exhaust valve 34 is pressed over the exhaust mechanism retention post 32 so as to reside in this circular region 40. The exhaust valve 34 is large enough in diameter to cover the arced slot 30. The central orifice 36 has a smaller diameter that the diameter of the top of the retention post 32 yet because of the elasticity of the polymer disc, it will stretch enough to pass over the top, widest section of the post 32 and then elastically deform to hug the post 32 and remain seated on the face of the transition section 31. The exhalation mechanism is comprised of the retention post 32, the exhaust valve 34, the depressed circular region 40 and the arced slot 30 in the preferred embodiment, however it is well known in the art that other designs of exhalation mechanisms may be employed. This style of externally mounted, externally opening exhalation mechanism accommodates the easy removal, cleaning and replacement of the exhaust valve 34. (See FIGS. 3 and 7)

Although, as described herein, the bottom sealing cap 6 is frictionally fit onto the chamber body 4 in an alternate embodiment, the bottom sealing cap 6 may have a first portion of a partial turn twist lock mechanism on its external surface that matingly engages its counterpart, a second portion of a partial turn twist lock mechanism located on the internal surface of the chamber body 4. In a second alternate embodiment, as is well know in the art, the first portion of a partial turn twist lock mechanism could be on the internal surface of the sealing cap 6 and matingly engage its counterpart, a second portion of a partial turn twist lock mechanism located on the external surface of the chamber body 4.

From the center of the bottom face of the sealing cap 6 extends normally, a hollow, circular nebulizer connection tube portion 22. Preferably this tube portion 22 has an 18 mm diameter, designed to matingly accommodate an internal engaging tapered tube on the nebulizer from which the medicated aerosol passes and can be drawn. There is a series of through penetrations 24 oriented on the bottom face of the sealing cap 6 adjacent the connection tube 22. This forms the bottom face of the sealing cap 6 into a multi port radial drain plate. These penetrations 24 are covered and sealed by the overlaying drain disc 8. (This drain disc 8 serves as a vacuum relief, drain check valve disc.) The central orifice 12 of the drain disc 8 aligns with the central orifice 50 of the hollow, circular nebulizer connection tube portion 22. This open connection from the nebulizer through the sealing cap's connection tube 22 to the chamber body 4 allows the unrestricted flow of medicated aerosol into the chamber's internal cavity.

When the internally mounted, internally opening drain disc 8 is inserted onto the raised inner lip 15 of the valve body and its outer peripheral edge is sandwiched/pinned between the chamber body 4 and the inner peripheral flange 16 of the sealing cap 6, the central orifice 12 of the drain disc 8 is positioned directly over and in alignment with the circular nebulizer connection tube portion 22. The disc 8 covers all of the penetrations 24 in the bottom face of the sealing cap 6. The disc's thickness is sufficient to allow upward deflection of the disc beginning at the edge of the orifice 12, tapering downward to its pinned outer periphery. As such, the drain disc 8 is free to rise and fall with the differential in pressure between the cavity of the chamber and the ambient room pressure caused by the inhalation and exhalation of the patient. The drain mechanism incorporates the drain disc 8 (with it central drain orifice 12), the lower peripheral circular lip 14 of the chamber body 4, the inner peripheral flange 16 of the sealing cap 6, and the penetrations 24. It is located on the sealing cap 6 but resides inside the chamber body 4 and opens internally. Although this internally opening, peripherally pinned, internally mounted drain mechanism is used in the preferred embodiment, it is well known in the art that other designs may be employed.

The drain mechanism has three purposes. First, when connected to a nebulizer, the drain mechanism allows the drainage of any condensed medicated aerosol in the chamber 2 to flow back down the nebulizer connection tube portion 22 into the nebulizer for reuse. Second, when the patient inhales, they draw in more that the normal 8 liters/min respiratory volume and more than the 105 cc volume of the chamber cavity. The differential in pressure created in the cavity causes the disc to deflect upward from its central orifice 12 breaking the seal over the penetrations 24 and allowing air to be drawn into the cavity through these penetrations 24 and sweep the medicated plume to the patient. This air carries the aerosol plume in the chamber 2 to the patient's lungs. The radial arrangement of the penetrations 24 on the drain plate also enables the air drawn up through the penetrations 24 as the drain disc 8 rises, to create the central vortex in the medicated aerosol plume as it is drawn up the chamber 2 into the patient. Third, as the drain disc 8 deflects upward, the slope created between the inner edge and outer edge of the disc prevents any of the accumulated condensed nebulizer fluid from dripping out of the penetrations 24.

The mouthpiece fitting 26 is in direct alignment with the arced slot port 30 on the short top arm 9. As the patient exhales, the differential pressure in the cavity will seal the drain mechanism and open the exhalation mechanism. As the patient inhales the differential pressure will seal the exhalation mechanism and open the drain mechanism. Thus the majority of the exhaled air passes harmlessly through the chamber 2 except for a small portion that aids in decreasing the MMAD of the aerosol plume by 15% from what is released by the attached nebulizer according to the combined efficiency enhancing mechanisms described herein.

In operation, a nebulizer has its outlet port frictionally engaged with the connection tube 22 of the sealing cap 6. The patient frictionally attaches a mouthpiece 7 to the mouthpiece fitting 26 of the chamber body 4. As the nebulizer generates the medical aerosol plume, it rises through the sealing cap 6 into the valve body 4 where it is constrained. Some condensation of the larger aerosol particles occurs within the chamber body 4. Once a sufficient plume resides in the chamber body 4 the patient inhales, opening the drain mechanism and closing the exhalation mechanism. This occurs because generally, patients using nebulizers inhale deeper than the average 8 liters/min normal respiratory rate and the chamber 2 has a 104 cc internal volume. This creates a negative differential pressure between the inside and outside of the chamber and the disc 8 of the exhalation mechanism lifts about its central orifice allowing air to enter the chamber body 4 through the penetrations 24. This incoming air is drawn through the penetrations 24 and central drain orifice 12 of the disc 8 establishes a central vortex in the chamber body 4. This aids in causing the heavier, larger medical aerosol particles to swirl outwards in the chamber body 4 and condense on the chamber's interior walls. This swirling vortex also aids in reducing the MMAD by concentrating the smaller aerosol particles into its center. The aerosol plume (charge) moves upward in the chamber body 4 towards the mouthpiece fitting 26. The smaller particles continue to concentrate within the center of the vortex while the larger, heavier aerosol particles continue to drift outward in the vortex and cannot navigate the non linear path to the mouthpiece fitting 26, colliding and condensing within the chamber by the mechanisms previously disclosed. With the drain disc 8 raised, condensed fluid is contained in the chamber body 4 and with exhaust valve 34 closed the only path for the medicated aerosol to take is into the patient's lungs. The losses of atomized aerosol to the environment is minimized.

When the patient exhales, a positive differential pressure between the inside and outside of the chamber is created and the exhaust valve 34 opens and dispels the unwanted patient's lung exhaust while simultaneously the drain disc 8 closes to seal the penetrations 24 and allows the condensed nebulizer fluid to flow back down the sealing cap into the nebulizer. Having the exhalation mechanism on the angled short, top arm 9 the patient's exhaled air has a straight path of least resistance to exit and it minimally disturbs the plume and very little of the plume is drawn outside of the chamber body 4.

As can be seen there are a plethora of design elements, both structural and mechanical that enact a multitude of efficiency mechanisms allowing for an improved level of medication delivery. These include a non linear, medicated aerosol holding and delivery chamber 2 without sealing valves at the aerosol inlet and outlet ends; a low pressure actuated, vacuum relief, drain check valve 8 at the inlet end of the chamber (in the internally opening, internally mounted drain mechanism); and an overpressure relief valve 34 at the outlet end of the chamber (in the externally opening, externally mounted exhalation mechanism). Using the novel design of the valved medical aerosol holding and delivery chamber 2 the numerous disclosed efficiency mechanisms result in an average of 15% decrease in the MMAD over the prior art devices. This allows for greater efficacy for a given amount of medical aerosol because of the increase in the inhaled dose. It is notable that even achieving the increased medical aerosol uptake results the chamber is non enclosed such that the aerosol medication housed therein is not constrained from release from said chamber body, whereas the prior art devices utilize sealing valves at their inlet and outlet ends.

As has been disclosed herein, the valved medical aerosol holding and delivery chamber by virtue of its chamber body size and configuration, internally opening, internal drain mechanism and externally opening, external exhalation mechanism, increases the medical efficiency in delivery of aerosols.

Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Having thus described the invention, what is claimed as new and desired to be secured by Letters Patent is as follows:

1. A valved, medical aerosol holding chamber comprising:
   a non-linear "V" shaped chamber body with an inlet end and an outlet end;
   a cap releasably engagable with said inlet end;
   an exhalation mechanism at said outlet end of said chamber body; and
   a drain mechanism at said inlet end of said chamber body.

2. The valved, medical aerosol holding chamber of claim 1 wherein said exhalation mechanism opens externally to the chamber body.

3. The valved, medical aerosol holding chamber of claim 2 wherein said drain mechanism opens internally to the chamber body and said chamber is non closed.

4. The valved, medical aerosol holding chamber of claim 3 further comprising:
   a hollow, generally circular in cross section, top arm having a first length;
   a hollow, generally circular in cross section, bottom arm having a second length;
   wherein said arms are connected so as to form an approximate 135 degree included angle between them, plus or minus 15 degrees, so as to form said non-linear "V" shaped chamber body.

5. The valved medical aerosol holding chamber of claim 4 wherein said exhalation mechanism comprises:
   a recessed region formed in an exterior surface of said top arm;
   an opening formed through said recessed region;
   a retention post extending from said recessed region; and
   a flexible exhalation disc with a first central orifice affixed about said retention post and physically conformed to fit in said recessed region.

6. The valved medical aerosol holding chamber of claim 4 wherein said drain mechanism comprises:
   a raised inner lip on said chamber body that resides concentric to an outer surface of the inlet end;
   a circular landing adjacent said lip;
   a drain disc with a raised flange and a second central orifice; and
   an inner peripheral flange on said cap;
   wherein when operational, said drain disc is sandwiched between said lip and said peripheral flange.

7. The valved medical aerosol holding chamber of claim 5 wherein said opening is crescent shaped.

8. The valved medical aerosol holding chamber of claim 5 wherein said drain mechanism comprises:
   a raised inner lip on said chamber body that resides concentric to an outer surface of the inlet end;
   a circular landing adjacent said lip;
   a drain disc with a raised flange and a second central orifice; and
   an inner peripheral flange on said cap;
   wherein when operational, said drain disc is sandwiched between said lip and said peripheral flange.

9. The valved medical aerosol holding chamber of claim 8 wherein said cap further comprises:
   a bottom face with a central first orifice formed therethrough;
   a series of second orifices formed therethrough said bottom face and arranged radially about said first orifice;
   an inner peripheral flange that abuts said drain disc; and
   a connection tube extending outward from said bottom face, adjacent said first orifice, said connection tube matingly engageable with a nebulizer.

10. The valved, medical aerosol holding chamber of claim 1 wherein said drain mechanism opens internally to the chamber body.

11. The valved medical aerosol holding chamber of claim 1 further comprising:
    a replaceable mouthpiece frictionally engagable with said outlet end.

12. The valved medical aerosol holding chamber of claim 11 wherein said mouthpiece has an internal drip tray formed thereon.

13. The valved medical aerosol holding chamber of claim 1 further comprising:
    a hollow, generally circular in cross section, top arm having a first length;
    a hollow, generally circular in cross section, bottom arm having a second length;
    wherein said arms are connected so as to form an approximate 135 degree included angle between them, plus or minus 15 degrees, so as to form said non-linear "V" shaped chamber body.

14. The valved medical aerosol holding chamber of claim 13 wherein said exhalation mechanism is affixed thereon an exterior surface of said chamber body.

15. The valved medical aerosol holding chamber of claim 14 wherein said drain mechanism is affixed thereon an interior surface of said chamber body when said cap is releasably engaged to said chamber body.

16. A valved, medical aerosol holding chamber comprising:
    a non-linear "V" shaped non closed chamber body with an inlet end and an outlet end;
    a cap releasably engagable with said inlet end;
    an exhalation mechanism affixed on said chamber body; and
    a drain mechanism at said inlet end of said chamber body.

17. The valved, medical aerosol holding chamber of claim 16 wherein said exhalation mechanism is adjacent said outlet end.

18. A non linear, open, holding and delivery medical aerosol chamber having aerosol inlet and outlet ends, without sealing valves comprising:
    a chamber body with an inlet end and an outlet end,
    an internally opening, internally mounted drain mechanism at said inlet end;
    an externally opening, externally mounted exhalation mechanism adjacent said outlet end; and wherein said chamber is non enclosed such that said aerosol medicant housed therein is not constrained from release from said chamber body.

19. The non linear, holding and delivery chamber of claim 18 wherein said drain mechanism utilizes a low pressure actuated, vacuum relief, drain check valve and said exhalation mechanism utilizes an overpressure relief valve at an outlet end of said chamber.

\* \* \* \* \*